United States Patent
Caponetti et al.

(10) Patent No.: US 10,583,082 B2
(45) Date of Patent: *Mar. 10, 2020

(54) COMPOSITION COMPRISING AT LEAST TWO DRY POWDERS OBTAINED BY SPRAY DRYING TO INCREASE THE STABILITY OF THE FORMULATION

(71) Applicant: Eratech S.R.L., Piacenza (IT)

(72) Inventors: Giovanni Caponetti, Piacenza (IT); Loretta Maggi, Piacenza (IT); Cristina Veneziani, Castel San Giovanni (IT); Paolo Ventura, Piacenza (IT); Laura Zanellotti, Piacenza (IT)

(73) Assignee: ZAMBON S.P.A., Bresso (MI) (IT)

( * ) Notice: Subject to any disclaimer, the term of this patent is extended or adjusted under 35 U.S.C. 154(b) by 0 days.

This patent is subject to a terminal disclaimer.

(21) Appl. No.: 14/783,247

(22) PCT Filed: Apr. 9, 2014

(86) PCT No.: PCT/EP2014/057200
§ 371 (c)(1),
(2) Date: Oct. 8, 2015

(87) PCT Pub. No.: WO2014/167023
PCT Pub. Date: Oct. 16, 2014

(65) Prior Publication Data
US 2016/0045434 A1    Feb. 18, 2016

(30) Foreign Application Priority Data
Apr. 10, 2013   (IT) .............................. MI2013A0572

(51) Int. Cl.
| | | |
|---|---|---|
| *A61K 9/00* | (2006.01) |
| *A61K 9/16* | (2006.01) |
| *A61K 31/167* | (2006.01) |
| *A61K 31/439* | (2006.01) |
| *A61K 31/58* | (2006.01) |
| *A61K 47/18* | (2017.01) |
| *A61K 47/26* | (2006.01) |

(52) U.S. Cl.
CPC .......... *A61K 9/0073* (2013.01); *A61K 9/0075* (2013.01); *A61K 9/1617* (2013.01); *A61K 9/1623* (2013.01); *A61K 31/167* (2013.01); *A61K 31/439* (2013.01); *A61K 31/58* (2013.01); *A61K 47/183* (2013.01); *A61K 47/26* (2013.01)

(58) Field of Classification Search
CPC .. A61K 9/0075; A61K 31/167; A61K 31/439; A61K 31/58; A61K 47/183; A61K 47/26; A61K 9/0073; A61K 9/1617; A61K 9/1623
See application file for complete search history.

(56) References Cited

U.S. PATENT DOCUMENTS

2008/0226736 A1* 9/2008 Caponetti ............ A61K 9/0075
424/489

FOREIGN PATENT DOCUMENTS

| WO | WO-02/00197 A1 | 1/2002 |
| WO | WO-2004/093848 A2 | 11/2004 |
| WO | WO-2012/051426 A2 | 4/2012 |

* cited by examiner

*Primary Examiner* — Jean P Cornet
(74) *Attorney, Agent, or Firm* — Polsinelli PC

(57) ABSTRACT

The present invention relates to inhalation formulations of drugs in the form of dry powder for inhalation administration deliverable as such with an inhaler and provided with high deliverability, respirability and stability. In particular, the invention relates to a pharmaceutical composition for inhalation in the form of powder comprising at least a first and a second powder, in which at least said first powder contains an active agent in an amount greater than 1% by weight with respect to the weight of said first powder. Both the powders comprise leucine in an amount ranging from 5 to 70% by weight with respect to the weight of each powder and a sugar in an amount ranging from 20 to 90% by weight with respect to the weight of each powder. The composition has a fine particle fraction (FPF) greater than 60% and a delivered fraction (DF) greater than 80.

14 Claims, No Drawings

COMPOSITION COMPRISING AT LEAST TWO DRY POWDERS OBTAINED BY SPRAY DRYING TO INCREASE THE STABILITY OF THE FORMULATION

CROSS REFERENCE TO RELATED APPLICATIONS

This application is a National Phase filing under 35 U.S.C. § 371 of PCT/EP2014/057200 filed on Apr. 9, 2014; and this application claims priority to Application No. MI2013A000572 filed in Italy on Apr. 10, 2013. The entire contents of each application are hereby incorporated by reference.

DESCRIPTION

The present invention relates to inhalation formulations of drugs in the form of dry powder for inhalation administration as such with an inhaler and having high deliverability, respirability and stability.

Inhalation therapy with aerosol preparations is used to administer active agents to the respiratory tract, in the mucosal, tracheal and bronchial regions. The term aerosol describes a preparation consisting of particles or fine droplets carried by a gas (usually air) to the site of therapeutic action. When the site of therapeutic action involves the pulmonary alveoli and small bronchi, the drug must be dispersed in the form of droplets or particles with an aerodynamic diameter of less than 5.0 μm.

When the target is the pharyngeal region, larger particles are more appropriate.

Conditions suitable for these treatments are represented by bronchospasm, inflammation, mucosal edema, pulmonary infections and the like.

Currently, administration of drugs in the deep lung region is obtained through inhalation devices such as:

nebulizers, in which the drug is dissolved or dispersed in the form of suspension and carried to the lung as nebulized droplets;

powder inhalers, capable of delivering the drug present in the inhaler as dry micronized particles; or pressurized inhalers, through which the drug—again in the form of droplets of solution or suspension—is carried to the deep lung region by an inert gas expanded rapidly in air by a pressurized canister.

In all these cases, technological problems have been encountered in the development of effective products that still limit the administration of drugs by inhalation.

From a clinical point of view, an ideal inhalation product should allow different administration methods to be used by the patient, since the inhalers described are generally suitable for different types of patients and administration conditions. In general, nebulizer therapy is prevalently used by elderly or pediatric patients, while therapy with dry powder or pressurized inhalers is more suitable for adults. However, the use of nebulizers is currently still considered effective, since the patient inhales the drug under rest conditions and without using forced inhalation, which is instead required for an inhalation powder. Instead, in the case of a pressurized inhaler, the product must be taken coordinating inspiration with activation of the device, to prevent the delivered particles from impacting on the bottom of the throat and failing to reach the deep lung.

For these reasons, the inhalation formulations used in these three types of inhalation devices are generally essentially very different from one another.

In the case of products for nebulizers, formulations are substantially constituted by solutions or suspensions containing as excipients salts, surfactants and preservatives to ensure isotonicity of the preparation, homogeneity of the particle size distribution in case of suspensions, and protection against microbial contamination.

In the case of pressurized preparations, the composition usually contains surfactants, propellants and co-solvents. In inhalation formulations in powder form, the excipients essentially consist of lactose with different particle size, used as carrier.

Some formulation or stability constraints in some cases have limited industrial development of inhalation products and, apart from corticosteroids, which exist substantially in all inhalation forms, in some bronchodilator and anti-cholinergic active agents some forms of administration are not available on the market. These limitations are particularly important since current respiratory therapy makes use of combinations of drugs of different kinds as the most effective technique and, in this regard, it has been possible to develop only a small number of corticosteroid-bronchodilator combinations, prevalently in the form of inhalation powder.

With regard to nebulized forms, the patient is left to extemporaneously combine different formulated products, which might even be incompatible with one another.

From a therapeutic point of view, it is therefore limiting for a patient not to be able to take the same drug in different conditions, such as at home, at work, while travelling and in an emergency. In the different situations indicated, a patient might be obliged to use different preparations containing different active agents.

The most important of the formulation problems encountered in the development of inhalation products concerns chemical stability in relation to atmospheric agents, which cause rapid degradation of the inhalation preparation and, consequently, decrease the shelf life of the product containing this preparation.

The stability of an inhalation product is particularly important, since it must be administered to the deep lung while maintaining its physical features for quantitative penetration of particles or droplets to the deepest regions thereof. Added to this is the fact that the number of excipients currently approved for inhalation administration and therefore acceptable in terms of toxicity for the pulmonary tissue is very limited.

The literature reports examples of dry inhalation powders with high dispersibility in air due to their low density. These powders are usually formulated with a high content of phospholipids, in particular dipalmitoylphosphatidylcholine (DPPC).

A powder of this kind is described in the patent application US2005/0074498 A1, relating to low density particles, with an internally hollow morphology, obtained by spray drying with the use of surfactants constituted by phospholipids in combination with a blowing agent). The hollow structure is described as resulting from the precise combination of the blowing agent and of the surfactant phospholipid. The document does not describe examples of similar morphology obtained without phospholipids. The use of phospholipids as surfactants determines the principal features of the product obtained and above all its sensitivity and stability in relation to atmospheric agents, which would be particularly influenced in this case by moisture. Moreover, the patent literature (US 2001/0036481 A1) indicates values of the phospholipid transition temperature (Tg) with humidity of 41° C. for DPPC, 55° C. for distearoylphosphatidylcholine (DSPC) and 63° C. for dipalmitoylphosphatidylethanolamine (DPPE), the three phospholipids most compatible with pulmonary administration.

The transition temperature is defined as the temperature required to cause a change in the physical state of the lipids, from the ordered gel phase in which the hydrocarbon chains are lying flat and closely packed, to the disordered liquid-crystalline phase in which the hydrocarbon chains are randomly oriented and fluid.

These Tg values are all much lower than the characteristic Tg value of amorphous lactose.

It is known that the closer the Tg is to the temperature of the environment in which the preparation is stored, the easier the transition will be. It is also known that in a system in which the main excipient is fluid and loosely packed, the molecular mobility of the components is very high, and consequently has a propensity to cause different chemical reactions and degradation of the active agents.

Therefore, the solution of producing porous particles for inhalation administration with phospholipids does not appear to be supported by reasonable scientific evaluation in relation to the long term stability of the product.

The aforesaid patent application, besides application as inhalation powder, also describes application of these particles in an inhaler device with a propellant gas. This administration would be impossible with a conventional nebulizer by dispersing the particles in water or aqueous solution, given the incompatibility of the materials with water, above all due to their tendency to float on the surface of the liquid or to dissolve slowly therein.

The concept of "high porosity" or "low density" has been used in a substantially equivalent manner in the cited patent applications.

In particular, the term "density" has been used not to refer to the absolute density of the particles, since this, measured with a helium pycnometer, would identify the density of the solid materials forming the powder and the particles according to the equation:

$$\rho = P/V \text{ (g/cc)}$$

but rather to refer to the apparent density (in some documents by others described as "envelope density") of the particle, considering its overall volume.

Given the technical difficulty of measuring this overall volume for each single particle, the cited patent applications have referred to volume (and subsequently to density) parameters of the powder as bulk volume and tapped volume.

The patent application WO 03/0350030 A1 describes the preparation of a kit for inhalation administration that considers the preparation of a solid dry form containing a drug prepared by freeze drying a solution. The process, also described through examples, present great difficulties in relation to industrial production and, above all, provide no guarantees of substantial improvement of the stability of the active agent over time. In fact, after freeze drying the drug added to the formulation is dispersed in an excipient network characterized by high porosity that cannot be modulated or modified through the process. Although it is useful from the point of view of rapid dissolution of the solid form, this porosity increases exposure of the drug to atmospheric agents and compromises its stability. In the specific case, no data are provided on the porosity of the freeze-dried products obtained in the examples, but literature data obtained through indirect measurements place the apparent density (corresponding to the bulk density of a powder) of formulated freeze-dried tablets containing sugars and surfactants between 0.05 and 0.2 g/cc.

The patent application CA2536319 describes a pharmaceutical composition obtained by spray drying, with a moisture content below 1%. According to what is indicated, this very low moisture content is necessary to ensure the stability of the composition, as a water content of over 1% in the powder would cause degradation of the pharmacologically active substances, resulting in a loss of efficacy of the composition. To reduce the level of moisture the composition is constituted by a large amount of mannitol, which however compromises the physical features of the powder considerably, increasing the particle size and decreasing the dose of powder delivered from the mouthpiece of the inhalation device used.

The problem of producing inhalation powders with high dispersibility has been solved through the engineering of particles that contain the drug as dispersed as possible.

Briefly, the technique used is that of producing essentially fine particles (geometric mean diameter greater than 4.0 µm) constituted by small amounts of active agent dispersed at molecular level inside an appropriate matrix of excipients capable of guaranteeing, through the spray drying preparation technique, the formation of a low density coarse particle.

This formulation approach requires the use of high percentages of excipients in the formulation, but enables small amounts of active agent to be contained in the composition.

For this reason, although these compositions solve the problem of aerodynamic performance, they fail to solve significant questions in terms of chemical stability.

The production of an inhalation powder in which the content % of active agent is high using a spray drying technique must instead be considered advantageous in terms of chemical stability. Considering the common active agents of respiratory therapy, in the majority of cases this content % of active agent would be too high to allow the production of an inhalation powder form, given the limited amount of powder that constitutes an individual dose of product.

In fact, this amount of powder is too small to be dosed reproducibly by any industrial device for producing individual doses of inhalation powders.

Therefore, the production of an inhalation powder that is stable both from a chemical and physical point of view must necessarily reconcile the need for stability of the active agents used with the need to ensure adequate aerosol performance in terms of deposition in the deep lung.

From the point of view of chemical stability, an ideal approach is represented by the production of dry powders containing large amounts of active agent in combination with a sugar capable of decreasing molecular mobility in the particles of powder and a hydrophobic excipient capable of limiting interaction with the external environment and absorption of water by the powder.

From the point of view of aerosol performance, the same powder must be characterized by an adequate particle diameter for inhalation administration and by a composition capable of facilitating particle disaggregation at the time of inhalation.

At the same time, convergence of physical composition features of the powder must coincide with the ability to divide the powder evenly using devices for the industrial preparation of products in the form of inhalation powder in individual doses or of multidose inhalers capable of drawing a relatively large dose from a storage chamber contained therein.

In the light of all of the aforesaid considerations, it would be advantageous to be able to produce a pharmaceutical composition for inhalation use in the form of dry powder that is stable and easy to administer with common dispensers for inhalation powders, while remaining easy to produce.

It would also be advantageous to obtain a solid composition in the form of dry powder, which can be used as diluent of inhalation powders in order to enable correct mixing of powders containing different active agents also in small amounts and at the same time maintains high stability of the formulation, preventing degradation of the active agents.

However, the problem of providing an inhalation formulation of drugs that is stable and administrable with common dispensers of inhalation powders, with features of high deliverability and respirability, and which can be produced with a commercially viable process, currently remains unsolved or unsatisfactorily solved.

According to the present invention, formulation is a combination of two or more different powders obtained according to the preparation procedure described by mixing, and HLSA and HLDA powders are powder with a high loading of active which are made according to the preparative spray drying procedure.

In the present description the wording "pharmaceutical composition" and "formulation" have the same meaning.

Therefore, a first aspect of the present invention is to provide a pharmaceutical composition for inhalation characterized in that it comprises at least a first and a second powder, in which at least said first powder comprises an active agent in an amount greater than 1% by weight with respect to the weight of said first powder, said first and second powder containing:
  a) leucine in an amount ranging from 5 to 70% by weight with respect to the weight of each powder;
  b) a sugar in an amount ranging from 20 to 90% by weight with respect to the weight of each powder;
in which said composition has a fine particle fraction (FPF) greater than 60% and a percentage of the dose delivered from the mouthpiece (DF) greater than 80%.

Another aspect of the invention is represented by a process for preparing said solid pharmaceutical composition comprising the following steps:
  a) providing at least a first powder obtained by spray drying comprising an active agent in an amount greater than 1% by weight with respect to the weight of the powder, leucine in an amount ranging from 5 to 70% by weight with respect to the weight of the powder, a sugar substantially amorphous after obtaining the powder by spray drying in an amount ranging from 20 to 90% by weight with respect to the weight of the powder;
  b) providing a second powder obtained by spray drying comprising leucine in an amount ranging from 5 to 70% by weight with respect to the weight of the powder, a sugar in an amount ranging from 20 to 90% by weight with respect to the weight of the powder;
  c) mixing the powders.

A further aspect of the invention is represented by a Kit for administration of a drug as inhalation powder, comprising a dosed amount of the composition according to the present invention and an inhalation device.

Another aspect of the present invention is represented by a solid composition for use as diluent of inhalation powders comprising a powder, characterized in that it comprises:
  a) leucine in an amount ranging from 5 to 70% by weight with respect to the weight of the powder;
  b) a sugar in an amount ranging from 20 to 90% by weight with respect to the weight of the powder;
in which said composition has an aerosol fine particle fraction (aerodynamic diameter <5,0 μm), greater than 60% and a percentage of the dose delivered from the mouthpiece (DF) greater than 80%.

According to the present invention, the term "active agent" is intended as any substance with a desired biological therapeutic efficacy.

Examples of active agents that can be administered by inhalation comprise: $\beta_2$ agonists; steroids such as glucocorticosteroids (preferably anti-inflammatory agents); anti-cholinergic agents; leukotriene antagonists; inhibitors of leukotriene synthesis; mucolytics; antibiotics, pain relievers in general such as analgesic and anti-inflammatory agents (including steroid and non-steroid anti-inflammatory agents); cardiovascular agents such as glucosides; respiratory agents; anti-asthma agents; bronchodilators; anti-cancer agents; alkaloids (i.e. rye ergot alkaloids) or triptans such as sumatriptan or rizatriptan that can be used to treat migraine; agents (i.e. sulfonylurea) used to treat diabetes and related dysfunctions; sleep inducing drugs such as sedative and hypnotic agents; psychic energizers; appetite inhibitors; anti-arthritis agents; anti-malaria agents; anti-epileptic agents; anti-thrombotic agents; anti-hypertensive agents; anti-arrhythmic agents; anti-oxidant agents; anti-psychotic agents; anxyolitics; anti-convulsant agents; anti-emetic agents; anti-infective agents; anti-hystamines; anti-fungus and anti-viral agents; drugs to treat neurological dysfunctions such as Parkinson's disease (dopamine antagonists); drugs to treat alcoholism and other forms of addiction; drugs such as vasodilators to treat erectile dysfunction; muscle relaxants; muscle contractors; opioids; stimulating agents; tranquilizers; antibiotics such as macrolides; aminoglycosides; fluoroquinolones and $\beta$-lactames; vaccines; cytokines; growth factors; hormones including birth-control drugs; sympathomimetic agents; diuretics; lipid regulating agents; anti-androgen agents; anti-parasitics; blood thinners; neoplastic agents; anti-neoplastic agents; hypoglycemic agents; nutritional agents and supplements; growth supplements; anti-enteric agents; vaccines; antibodies; diagnostic and contrast agents; or mixtures of the above substances (e.g. combinations for the treatment of asthma containing steroids and $\beta$-agonists).

The aforesaid active agents belong to one or more structural classes, including, but not limited to, small molecules (preferably small insoluble molecules), peptides, polypeptides, proteins, polysaccharides, steroids, nucleotides, oligonucleotides, polynucleotides, fats, electrolytes and the like.

Specific examples include $\beta_2$ agonists salbutamol, salmeterol (e.g. salmeterol xinafoate), formoterol and formoterol fumarate, fenoterol, steroids such as beclomethasone dipropionate, budesonide, fluticasone (e.g. fluticasone propionate). In relation to peptides and proteins, the present invention also includes synthetic, recombinant, native, glycosylated and non glycosylated peptides and proteins, biologically active fragments and analogs.

Active agents for which an immediate release into the bloodstream is particularly advantageous to obtain a rapid pharmacological effect include those to be used to treat migraine, nausea, insomnia, allergic reactions (including anaphylactic reactions), neurological and psychiatric disorders (in particular panic attacks and other psychoses or neuroses), erectile dysfunction, diabetes and related diseases, heart diseases, anti-convulsive agents, bronchodilators and active agents to treat pain and inflammation.

According to the present invention, vaccines constituted by antibodies, cells, corpuscles and cellular portions can also be administered.

Other examples of active substances are steroids and their salts, such as budesonide, testosterone, progesterone, flunisolide, triamcinolone, beclomethasone, betamethasone, dexamethasone, fluticasone, methylprednisolone, prednisone, hydrocortisone and the like; peptides such as cyclosporine and other water-insoluble peptides; retinoids such as cis-retinoic acid, 13-trans-retinoic acid and other derivatives of vitamin A and of beta-carotene; vitamins D, E and K and their precursors and water-insoluble derivatives; prostaglandins, leukotriens and their activators and inhibitors including prostacyclin, prostaglandins E1 and E2, tetrahydrocannabinol, pulmonary surfactant lipids; lipid-soluble anti-oxidants; hydrophobic antibiotics and chemotherapic drugs such as amphotericin B, adriamycin and the like.

In particular, according to the present invention the active agent is a degradable active agent, i.e. a substance capable of undergoing degradation processes as a function of the amount of water present in the formulation.

According to the present invention, the term "sugar" is intended as monosaccharides with 5 or more carbon atoms, disaccharides, oligosaccharides or polysaccharides and also polyols with 5 or more carbon atoms (often also defined as sugar-alcohol)

Examples of sugars that can be administered by inhalation comprise: lactose, threalose, sucrose, maltose, melibiose, cellobiose, mannitol, dextrins, maltodextrins, sorbitol, galactitol, iditol, volemitol, fucitol, inositol, maltitol, lactitol, isomalt, maltotriitol, maltotetraitol, polyglycitol. The amount of sugar present in the powders contained in the pharmaceutical composition of the present description ranges from 20 to 90% by weight with respect to the weight of each powder, is preferably present in an amount ranging from 20 to 80% by weight with respect to the weight of each powder, even more preferably in an amount ranging from 40 to 80% by weight with respect to the weight of each powder.

According to the present invention the powders contained in the pharmaceutical composition of the present description include a hydrophobic substance to reduce moisture sensitivity. This hydrophobic substance is leucine, which also facilitates particle disaggregation. Leucine is present in an amount ranging from 5 to 70% by weight with respect to the weight of each powder. Preferably the amount of leucine present in the powders contained in the pharmaceutical composition ranges from 15 to 70% by weight with respect to the weight of each powder, even more preferably from 18 to 55% by weight with respect to the weight of each powder.

According to the present invention the first and the second powder that constitute the composition comprise a surfactant in an amount ranging from 0.2 to 2% by weight with respect to the weight of each powder, preferably in an amount ranging from 0.4 to 0.8% by weight with respect to the weight of each powder.

The surfactant of the pharmaceutical composition according to the invention can be selected from the various classes of surfactants for pharmaceutical use.

Surfactants suitable to be used in the present invention are all those substances characterized by medium or low molecular weight containing a hydrophobic moiety, generally readily soluble in an organic solvent but weakly soluble or totally insoluble in water, and a hydrophilic (or polar) moiety, weakly soluble or completely insoluble in an organic solvent but readily soluble in water. Surfactants are classified according to their polar moiety. Therefore, surfactants with a negatively charged polar moiety are called anionic surfactants, while cationic surfactants contain a positively charged polar moiety. Uncharged surfactants are generally called non ionic, while surfactants with both a positive and negative charge are called zwitterionic. Examples of anionic surfactants are represented by the salts of fatty acids (better known as soaps), sulphates, sulphate ethers and phosphate esters. Cationic surfactants are frequently based on polar groups containing amino groups. The most common non ionic surfactants are based on polar groups containing oligo-(ethylene-oxide) groups. Zwitterionic surfactants are generally characterized by a polar group constituted by a quaternary amine and a sulphuric or carboxylic group.

Specific examples of this application are represented by the following surfactants: benzalkonium chloride, cetrimide, docusate sodium, glyceryl monooleate, sorbitan esters, sodium lauryl sulphate, polysorbates, phospholipids, biliary salts.

Non ionic surfactants, such as polysorbates and polyoxyethylene and polyoxypropylene block copolymers, known as "Poloxamers", are preferred. Polysorbates are described in the CTFA International Cosmetic Ingredient Dictionary as mixtures of sorbitol and sorbitol anhydride fatty acid esters condensed with ethylene oxide. Particularly preferred are non ionic surfactants of the series known as "Tween", in particular the surfactant known as "Tween 80", a polyoxyethylene sorbitan monooleate available on the market.

The presence of a surfactant, and preferably of Tween 80, is necessary to reduce the electrostatic charges found in powders without it, flow of the powder and maintenance of a homogeneous solid state without initial crystallization.

According to the present invention, the term "inhalable" is intended as a powder suitable for pulmonary administration. An inhalable powder can be dispersed and inhaled by means of an appropriate inhaler, so that the particle can enter the lungs and alveoli to provide the pharmacological features of the active agent of which it is formed. A particle with aerodynamic diameter of less than 5.0 μm is normally considered inhalable.

The term "amorphous" according to the present invention is intended as a powder that contains less than 70% of crystalline fraction, more preferably less than 55%. The pharmaceutical composition described in this text has a ratio between the amount of powder in amorphous form that constitutes the composition expressed by weight and the amount of sugar present in the composition expressed by weight ranging from 0.8 to 2.0. This ratio indicates that the sugar present in the powder is a substantially amorphous sugar, which therefore has a crystalline fraction of less than 50%. This enables the sugar to coordinate the water present in the composition, preventing it from being available to hydrolyze the active agent, thereby making it ineffective.

In a further embodiment, the pharmaceutical composition according to the present invention comprises a third powder comprising an active agent, according to the previously indicated features, in an amount greater than 1% by weight with respect to the weight of said third powder, leucine in an amount ranging from 5 to 70% by weight with respect to the weight of said third powder, a sugar in an amount ranging from 20 to 90% by weight with respect to the weight of said third powder.

With a pharmaceutical composition as described in this second embodiment, it is possible to obtain a pharmacologically active composition that can comprise the combination of two or more different active agents capable of acting synergically, or simply acting simultaneously in the application site, so as to reduce the number of administrations.

The term "fine particle fraction (FPF)" is intended as the fraction of powder, with respect to the total delivered by an inhaler, which has an aerodynamic diameter (dae) of less than 5.0 μm. The characterization test that is performed to evaluate this property of the powder is the Multi Stage Liquid Impinger (MSLI) test, as described in the European Pharmacopoeia current ed. The conditions for performing this test consist in subjecting the powder to an inhalation through the inhaler such as to generate a flow of 60 litres/min. This flow is obtained by producing a pressure drop of 2 KPa in the system.

The term "delivered fraction (DF)" is intended as the fraction of active agent, with respect to the total loaded, delivered by a powder inhaler in standard inhalation conditions.

The characterization test performed to evaluate this property of the powder is the DUSA test, as described in the European Pharmacopoeia current ed. The conditions for performing this test consist in subjecting the powder to an inhalation through the inhaler such as to produce a pressure drop of 4 KPa in the system.

The preferred production process of the powder according to the invention is spray drying starting from a solution of leucine, of a sugar and a surfactant in which the drug, if present, is dissolved or dispersed as suspension or emulsion.

The preferred particle size for this powder provides that at least 50% of the size distribution (X50) is below 5 μm, preferably below 3 μm, more preferably below 2.0 μm, also to increase the surface area optimizing deep lung deposition.

According to the present invention, the powder that constitutes the pharmaceutical composition is a substantially dry powder, i.e. a powder with a moisture content of less than 10%, preferably less than 5%, more preferably below 3%. This dry powder preferably has no water capable of hydrolyzing the active agent making it inactive. The amount of moisture present in the composition is controlled by the presence of leucine, which limits the content due to its hydrophic features, both in the step to produce the powder and in the subsequent handling steps, and of sugar, which traps the water in a structure that becomes increasingly rigid over time, preventing the water from hydrolyzing the active agent.

The process for preparing the pharmaceutical composition according to the invention substantially comprises the operations of:

a) providing at least a first powder obtained by spray drying comprising an active agent in an amount greater than 1% by weight with respect to the weight of the powder, leucine in an amount ranging from 5 to 70% by weight with respect to the weight of the powder, a sugar substantially amorphous after obtaining the powder by spray drying in an amount ranging from 20 to 90% by weight with respect to the weight of the powder;

b) providing a second powder obtained by spray draying comprising leucine in an amount ranging from 5 to 70% by weight with respect to the weight of the powder, a sugar substantially amorphous after obtaining the powder by spray drying in an amount ranging from 20 to 90% by weight with respect to the weight of the powder;

c) mixing the powders.

In particular the production process of the composition, in step a) and b) of obtaining the powders by spray drying, consists of a series of operations illustrated below: For step a):

preparing a first phase (A) in which an active agent is present in an appropriate liquid medium;

preparing a second phase (B) in which the leucine, the sugar and surfactants are dissolved or dispersed in an aqueous medium;

mixing said phases (A) and (B) to obtain a third phase (C) in which the liquid medium is homogeneous;

drying said phase (C) in controlled conditions to obtain a dry powder with particles having a size distribution with median diameter of less than 10.0 μm;

collecting said dry powder.

Phase (A) can be either a suspension of the active agent in an aqueous or non aqueous medium, or a solution of the active agent in an appropriate solvent.

Preparation of a solution is preferable, and the organic solvent is selected from those soluble in water. In this case, phase (C) is also a solution of all the components of the desired composition.

Instead, when phase (A) is a suspension of the hydrophobic active agent in an aqueous medium, phase (C) is also a suspension in an aqueous medium, which will contain the dissolved soluble components such as the excipients and surfactants.

The drying operation consists of eliminating the liquid medium, solvent or dispersant, from phase (C), to obtain a dry powder with the desired dimensional features. This drying is preferably obtained by spray drying. The features of the nozzle and the process parameters are selected so that the liquid medium is evaporated from the solution or suspension (C) and a powder with the desired particle size is formed.

Step c) of the process for preparing the pharmaceutical composition instead consists of physical mixing of the powders obtained by spray draying using the most common mixing techniques, i.e. rotating mixers such as Turbula, V-mixer, cylinder, double cone, cube mixers or stationary mixers used only for mixing, such as planetary, nautamix, sigma, ribbon mixers or mixer-granulators, such as Diosna. Besides these mixers, the powders could also be mixed with devices normally used to mix liquids, such as Ultra Turrax or Silverson and, ultimately, also inside fluid bed granulation apparatus.

As already indicated above, a further aspect of the present invention is that of obtaining a solid composition for use as diluent of inhalation powders, called bulking agent (BA), comprising leucine in an amount ranging from 5 to 70% by weight with respect to the weight of the powder; a sugar in an amount ranging from 20 to 90% by weight with respect to the weight of the powder, in which said composition has a fine particle fraction (FPF) greater than 60% and a percentage of the dose delivered from the mouthpiece (DF) greater than 80%. This composition can be used as diluent of inhalation powders, i.e. as powder capable of diluting the powder containing the active agent and at the same time improving both the aerodynamic performance of the final composition, and improving the stability of the composition.

In particular, for some active agents, with very limited doses within the pharmaceutical composition to be administered, it is necessary to obtain an inert powder from a pharmacological point of view, capable of facilitating the operations to divide it in the predetermined pharmaceutical form.

The production process of the bulking agent, i.e. step b) of the preparation process, is substantially similar to the process for preparing the composition containing the active agent (phase a)), in particular, this process consists of the following operations:

preparing a first phase (A) in which the leucine, the sugar and surfactants are dissolved or dispersed in an aqueous medium;

drying said phase (A) in controlled conditions to obtain a dry powder with particles with a size distribution having a median diameter of less than 10.0 µm;

collecting said dry powder.

EXAMPLES

The methods for preparing the powders that constitute the pharmaceutical composition and for preparing the solid composition for use as diluent (hereinafter bulking agent) of the present invention will now be described.

Preparation of the Individual Powders.

The powders containing the active agents and the bulking agent were obtained by spray drying, a drying technique used to obtain powders with uniform and amorphous particles from solutions of active agents and excipients in appropriate solvent or mixture of solvents.

For the powders described the solvents used are water and ethyl alcohol in a fixed ratio of 70/30. The concentration of dissolved solids is 1% w/v for powders containing the active agent and 2% w/v for the bulking agent.

In the case of the powder containing formoterol fumarate as active agent and bulking agent, all the components of the powder were dissolved in water and the solution thus obtained was added to the portion of ethyl alcohol slowly at 25° C.

For the powder containing Budesonide as active agent, the active agent was dissolved separately in the alcohol portion to which the aqueous solution of the excipients was added to obtain a single water-alcohol solution.

The water-alcohol solution thus obtained was processed by means of a Buchi Mod. B290 spray dryer, using an open cycle with the following parameters:

nozzle diameter 0.7 mm
atomization gas nitrogen
atomization pressure 4 bar
drying gas air
aspiration 100% (35 m3/h)
inlet temperature 170° C.
feed speed 8% (2.4 ml/min)
Powder collection system: cyclone separator with glass collection vessel (External diameter: 8,5 cm. Height: 30,5 cm)
Outlet filter: nylon sleeve At the end of the drying process the powder collection step was performed in controlled temperature and humidity conditions: temperature <25° C., relative humidity <35%.

The powders were packaged immediately after production in borosilicate glass vials inserted in a double aluminum foil bag heat-sealed under partial vacuum (30%).

Preparation of the Mixtures.

The formulations described in the examples were produced by mixing powders containing the active agents and bulking agent. Regardless of the quantitative ratios between initial powders, a layer-wise mixing technique was used, depositing the powder containing the active agent between two layers of bulking agent in the mixing container. The powders were mixed using an Ultra Turrax T10 mixer for a mixing time of 5 minutes considered sufficient for the 3.5 g of powder of the batches produced. Uniformity of the content was controlled with titre analysis on 10 samples taken from different points of the bulk.

The powders were divided in sealed vials and stored inside a double aluminum foil bag heat sealed with partial vacuum (30%).

The operations of mixing and dividing in vials were carried out inside a glove box in controlled humidity and temperature conditions; max temperature 20° C. and environmental relative humidity <35%.

Storage Conditions for Accelerated Stability Study.

The powders studied, packaged as described above, during the accelerated stability study were stored in an oven at a temperature of 40° C. and relative humidity 13%.

At each time interval established by the study, the samples corresponding to the stability point were taken, left to cool until reaching room temperature, opened in controlled conditions in a glove box (temperature <20° C., RH<35%) and analyzed as established in the protocol.

Characterization of the Powder: Particle Size Analysis.

The powders obtained were characterized in terms of dry particle size using a Sympatec Helos light scattering device that analyzes the particle size according to the Fraunhofer theory and equipped with RODOS disperser.

The instrument was suitably calibrated with reference material and prepared following the instructions provided in the instrument user manual.

After appropriate cleaning before analysis, an amount of powder for each batch produced was analyzed without any preliminary preparation of the sample.

The dispersion gas used was compressed air suitably cleansed of particles.

The test method specified therefore provides for compliance with the following measures in relation to the sample, to the powder disperser and to the light scattering analyzer.

Sample
  size: about 100 mg
  feed procedure: with a spatula
  pre-treatment of the sample: none
RODOS Disperser
  Model M ID-NR 230 V/Hz 24 Va
  Dispersion pressure: 3 bar
Light Scattering Analyzer
  Model: Helos
  Test method: Fraunhofer
  Software version: Windox 4.0
  Test lens: R1 (0.1-35 µm)
  Minimum optical concentration: 1%
  Activation threshold: minimum optical concentration detectable 1% for max 30 seconds of time and with at least 100 ms of exposure of the sample.

All the tests were conducted in controlled temperature and humidity environments, temperature <25° C. and relative humidity <50% RH.

Size analysis provides volume median diameter (VMD) values of the population of particles in the sample of powder.

Characterization of the Powder: Residual Moisture Content.

The residual moisture content in the powder was measured using the Karl Fischer coulometric system method.

The C20 Compact Karl Fischer Coulometer Mettler Toledo titrator was used for this purpose, which uses as reagent HYDRANAL®-Coulomat AG.

The sample powders were accurately weighed in an amount of around 15-20 mg and the weight was recorded in the parameters of the sample. Titration was started immediately after adding the sample to the reagent bath.

At the end of the test, the instrument indicates directly the percentage of water contained in the sample.

Characterization of the Powder: Determination of Titre and Related.

The HPLC (High Performance Liquid Chromatography) test method was used to determine the content of the active agents and their related substances.

The test method is characterized by the following parameters:

Solvent: 50/50 methanol/phosphate buffer pH 2.7 25 mM

Mobile phase: acetonitrile/phosphate buffer pH 2.9 2.82 mM gradient elution

| Time (min) | % ACN | % buffer pH 2.9 | Flow (ml/min) |
|---|---|---|---|
| 0 | 22 | 78 | 0.5 |
| 2.5 | 22 | 78 | 0.5 |
| 3.0 | 41 | 59 | 0.7 |
| 8.0 | 41 | 59 | 0.7 |
| 10.0 | 70 | 30 | 0.7 |
| 12.0 | 22 | 78 | 0.6 |
| 15.0 | 22 | 78 | 0.6 |

Injection volume: 20 µL

Analysis column: Agilent Poroshell 120 EC-C18, 100 mm×3.0 mm, 2.7 µm

Column temperature: 30° C.

Wavelength: 220 nm (Formoterol Fumarate) and 240 nm (Budesonide)

Retention time: 2.4 min (Formoterol Fumarate) and 8.0 min (Budesonide)

An HPLC Agilent model 1200 with diode array type detector, model G1315C was used for the test.

The samples for analysis were obtained by dissolving in the solvent an amount of powder such as to obtain a concentration of 160 µg/ml for the Budesonide and 4.5 µg/ml for the Formoterol Fumarate, as for the reference solution.

The reference solution was injected three consecutive times before the sample to determine the precision of the system expressed as relative standard deviation percentage (RSD %), which must be less than 2%.

The active agent content is obtained by calculating the ratio of the areas with respect to the reference solution at known concentration. The degradation of the product is calculated as ratio between the sum of the areas of all the analysis peaks corresponding to the degradation products and the active agent taken as reference. All the analysis peaks whose chromatogram area was greater than 0.1% of the area of the active agent are counted in the sum of the degradation products.

Characterization of the Powder: Differential Scanning Calorimetry.

Differential scanning calorimetry or DSC is a thermoanalytical technique used to determine chemical and physical phenomena with endothermic or exothermic effect in a sample, such as variations in phase, loss of water, chemical reactions.

In DSC the sample is heated with constant heating speed and the amount of heat required to raise its temperature is a function of its thermal capacity. Each endothermic or exothermic phenomenon causes a reversible or irreversible change in the thermal capacity of the material and can be detected as a variation of the baseline of the thermogram.

Powders containing amorphous lactose show during heating a typical decrease in thermal capacity corresponding to the glass transition of the lactose from amorphous solid state to a metastable state that rapidly leads to its crystallization, characterized by an exothermic peak. The temperature corresponding to these phenomena varies as a function of the composition of the sample and of the environmental conditions in which the sample is stored and prepared.

The samples were prepared in a controlled environment (temperature <20° C., relative humidity 35-30%). 40 uL aluminum standard crucibles for DSC were filled with a weighed amount of powder between 1 mg and 3 mg and sealed with specific lid.

Calorimetry testing of the samples in question was carried out by subjecting the samples to a heating ramp from 20 to 200° C. with a temperature increase of 10° C./min.

The test gives a thermogram in which the thermal events that accompany progressive heating of the sample are visible.

The glass transition (Tg) is identifiable with a decreasing step, at times followed by an increase in the baseline caused by relaxation enthalpy. During evaluation of the thermograms the onset temperature of the phenomenon (Tg onset) is calculated, regardless of the sample size. The glass transition temperature is a stability index of the powder as it is a prelude to crystallization, which takes place above 100° C. The exothermic crystallization peak can be integrated and the area subtended by the curve is an index of the amorphous fraction of the sample.

Characterization of the Powder: Respirability Test with MSLI.

The Multi Stage Liquid Impinger (MSLI) is a device that simulates in vitro pulmonary deposition of an inhalation formulation. A inhalation formulation, delivered by appropriate inhaler and conveyed into the device by aspiration, is deposited in the various stages connected in series of the impactor as a function of its aerodynamic features, such as particle size, density, shape. Each stage of the MSLI corresponds to an interval of aerodynamic particle sizes of the powder deposited therein and the aerodynamic size distribution of the powder is obtained using HPLC testing to determine the amount of active agent in each stage, making it possible to calculate the mass median aerodynamic diameter (MMAD) and the respirable fraction (also known as fine particle fraction, FPF), considered according to the European Pharmacopoeia with aerodynamic diameter <5.0 µm.

For the respirability test, the powders of the formulations of the examples were partitioned into Size 3 HPMC capsules and delivered from RS01 powder inhaler—model 7 monodose, code 239700001AB (Aerolizer-Plastiape S.p.A.).

The device was assembled following the instructions for use and the indications of the European Pharmacopoeia.

For test purposes, it is necessary to deliver 10 powder capsules for each respirability test. The tests were conducted at a flow of 60 Lpm for 4 seconds deriving from a pressure drop of 2 KPa in the system.

The following aerodynamic diameter cut-offs correspond to this flow value for each stage.

stage 1: >13 µm
stage 2: from 13 µm to 6.8 µm
stage 3: from 6.8 µm to 3.1 µm
stage 4: from 3.1 µm to 1.7 µm
stage 5 (filter): <1.7 µm The respirable fraction (Fine Particle Fraction) comprises particles with aerodynamic diameter of less than 5 µm and is calculated using specific software (CITDAS Copley).

The aerodynamic parameters of an inhalation formulation subjected to MSLI analysis are expressed in terms of:

Delivered Fraction (DF): i.e. the percentage of the dose of active agent delivered from the mouthpiece of the inhaler Fine Particle Dose (FPD): respirable dose of active agent, having aerodynamic diameter <5.0 µm.

Fine Particle Fraction (FPF): respirable fraction (aerodynamic diameter <5.0 μm) of active agent expressed as percentage of the amount delivered.

Mass Median Aerodynamic Diameter (MMAD): median aerodynamic diameter of the particles delivered.

Quantitative determination of the active agent in each stage was performed by HPLC using the test method for content and degradation products.

Example 1

Example 1 was conducted producing powders containing Formoterol Fumarate, which is an active agent sensitive to the presence of free water in the formulation.

Together with formoterol powders, powders containing different amounts of leucine and lactose or mannitol were produced.

The example highlights the protective effect of lactose against formoterol, this protective effect is explained considering that lactose is capable of exerting a scavenger effect against free water present in the formulation.

To demonstrate this, powders of 3 types were produced:
A powder containing exclusively formoterol and leucine
2 powders with different lactose contents together with formoterol and leucine
2 powders in which lactose was substituted by a different pharmaceutical excipient widely utilized by spray drying: mannitol The powders with lactose tend to acquire moisture over time, with consequent decrease of Tg, but degradation over time is limited. This limited degradation is presumably due to a scavenger effect produced by the lactose against the water, which is thus trapped in a rigid structure and prevented from reacting with the other components. Differently, the powders without lactose which was already crystalline, undergoes chemical degradation.

Of the two powders containing lactose, the one with 50% is better, as it is more stable over time.

TABLE 1A

| | | Formoterol | | | Water content (%) | |
|---|---|---|---|---|---|---|
| Ex. | Active | (%) | Leucine % | Sugar | T0 | T28 days |
| 1 | Formoterol | 5 | 95 | NO Sugar | 0.9 | 0.9 |
| 2 | Formoterol | 5 | 70 | Lactose | 1.4 | 1.8 |
| 3 | Formoterol | 5 | 45 | Lactose | 2.1 | 2.7 |
| 4 | Formoterol | 5 | 70 | Mannitol | 0.9 | 0.9 |
| 5 | Formoterol | 5 | 45 | Mannitol | 1.0 | 0.9 |

TABLE 1B

| | Tg (° C.) | | P. size (VMD) | | Degradation products (%) | |
|---|---|---|---|---|---|---|
| Ex. | T0 | T28 days | T0 | T28 days | T0 | T28 days |
| 1 | Not detected | Not detected | 2.6 | 2.7 | 0.6 | 0.9 |
| 2 | 62.7 | 56.9 | 2.0 | 1.9 | 0.4 | 0.4 |
| 3 | 66.3 | 57.5 | 1.6 | 1.6 | 0.3 | 0.3 |
| 4 | Not detected | Not detected | 2.3 | 2.2 | 0.2 | 1.6 |
| 5 | Not detected | Not detected | 1.6 | 1.6 | 0.1 | 1.4 |

Example 2

The example was conducted producing powders containing Budesonide as active agent (defined as HLSA Bud in the table) formulated with lactose and leucine at two different quantitative levels.

Following preparation of the powders of example 6 and 9, these were mixed with 2 types of bulking agent powders (defined as BA in the table), i.e. of powder containing leucine and lactose but with no active agent.

The presence of leucine in different amounts ranging from 0% to 20% serves to highlight the properties of disaggregating agent that this takes place in the formulation, with positive effects on parameters such as Delivered Fraction and Fine Particle Fraction.

This second part of the study highlights the ability of the Bulking Agent to promote complete emptying of the capsule.

Nevertheless, the composition of the Bulking agent is critical, since a Bulking Agent that has too much leucine produces effects of chemical degradation of the active agent.

According to the present invention, the powder is acceptable, i.e. is considered within the optimal parameters for inhalation administration, when:

the degradation products are less than 0.5% on the total of active agent, at the time T2 (degradation products T2<0.5% tot);

the Delivered Fraction, i.e. the percentage of the dose of active agent delivered from the mouthpiece of the inhaler, is greater than 90% at the time T2 (ED % T2>90%);

the Fine Particle Fraction, i.e. the amount of fine particles below 5 μm, is greater than 60% at the time T2. (FPT T2>60%).

TABLE 2A

| | | | HLSA Bud (composition %) | | | BA (composition %) | | | Powder mixture | |
|---|---|---|---|---|---|---|---|---|---|---|
| Ex. | Active | Bud. | Leucine | Lactose | Tween 80 | Leucine | Lactose | Tween 80 | HLSA Bud (mg) | BA (mg) |
| 6 | Budesonide | 8 | 0.0 | 91.5 | 0.5 | | | | 5.0 | 0.0 |
| 7 | Budesonide | 8 | 0.0 | 91.5 | 0.5 | 50.0 | 49.5 | 0.5 | 5.0 | 15.0 |
| 8 | Budesonide | 8 | 0.0 | 91.5 | 0.5 | 99.5 | 0.0 | 0.5 | 5.0 | 15.0 |
| 9 | Budesonide | 8 | 20.0 | 71.5 | 0.5 | | | | 5.0 | 0.0 |
| 10 | Budesonide | 8 | 20.0 | 71.5 | 0.5 | 50.0 | 49.5 | 0.5 | 5.0 | 15.0 |
| 11 | Budesonide | 8 | 20.0 | 71.5 | 0.5 | 99.5 | 0.0 | 0.5 | 5.0 | 15.0 |

TABLE 2B

| | Water content (%) | | | Particle Size (μm) | | | Active content % | | |
|---|---|---|---|---|---|---|---|---|---|
| Ex. | T0 | T1 | T2 | T0 | T1 | T2 | T0 | T1 | T2 |
| 6 | 2.8 | 3.2 | 2.9 | 1.9 | 2.1 | 2.6 | 101.2 | 96.7 | 102.5 |
| 7 | 2.6 | 3.2 | 3.1 | 1.8 | 1.9 | 2.2 | 105.7 | 104.1 | 105.6 |
| 8 | 0.8 | 1.6 | 1.1 | 2.6 | 2.7 | 2.8 | 101 | 101.3 | 101.1 |
| 9 | 2.5 | 3.6 | 3 | 1.5 | 1.5 | 1.7 | 99.2 | 100.9 | 100.6 |
| 10 | 2.6 | 3.2 | 2.8 | 1.7 | 1.7 | 1.8 | 100.5 | 100.7 | 100.7 |
| 11 | 0.7 | 1.2 | 1.3 | 2.7 | 2.7 | 2.8 | 99.3 | 101.5 | 100.7 |

The active content measured after 1 and 2 months was variable but always between 95 and 110% of the theoretical content.

TABLE 2C

| | Degradation (%) | | | DF (%) | | | FPF (%) | | |
|---|---|---|---|---|---|---|---|---|---|
| Ex. | T0 | T1 | T2 | T0 | T1 | T2 | T0 | T1 | T2 |
| 6 | 0.0 | 0.2 | 0.2 | 81.8 | 81.4 | 84.6 | 51.2 | 38.0 | 36.7 |
| 7 | 0.1 | 0.2 | 0.3 | 95.4 | 94.6 | 97.1 | 44.6 | 40.0 | 42.6 |
| 8 | 0.0 | 1.2 | 1.9 | 94.9 | 95.4 | 94.9 | 34.4 | 46.7 | 43.4 |
| 9 | 0.2 | 0.2 | 0.3 | 85.2 | 84.1 | 85.2 | 71.0 | 78.4 | 73.6 |
| 10 | 0.2 | 0.3 | 0.3 | 93.8 | 95.8 | 95.2 | 70.5 | 71.4 | 65.8 |
| 11 | 0.2 | 1.1 | 1.8 | 93.4 | 96.4 | 93.9 | 42.1 | 62.0 | 63.3 |

This further part of the study highlights the capacity of the Bulking agent to promote complete emptying of the capsule.

Nevertheless, the composition of the Bulking agent is critical since a Bulking Agent with too much leucine produces effects of chemical degradation of the active agent.

According to the present invention the powder is acceptable, i.e. is considered within the optimal parameters for inhalation administration, when:

the degradation products are less than 1% of the total active agent, at the time T0 (degradation products T0<1% tot);

the Delivered Fraction (DF), i.e. the percentage of the dose of active agent delivered from the mouthpiece of the inhaler, is greater than 80% at the time T3 (ED % T3>80%);

the Fine Particle Fraction, i.e. the amount of fine particles with aerodynamic diameter of less than 5.0 μm, is greater than 60% at the time T0 and at the time T3 (FPF T0 and T3>60%).

TABLE 3A

| | | | HLSA Bud (composition %) | | | BA (composition %) | | | Powder mixture | |
|---|---|---|---|---|---|---|---|---|---|---|
| Ex. | Active | Bud. | Leucine | Lactose | Tween 80 | Leucine | Lactose | Tween 80 | HLSA Bud (mg) | BA (mg) |
| 12 | Budesonide | 8 | 0.0 | 91.5 | 0.5 | | | | 5.0 | 0 |
| 13 | Budesonide | 8 | 50.0 | 41.5 | 0.5 | | | | 5.0 | 0 |
| 14 | Budesonide | 8 | 91.5 | 0.0 | 0.5 | | | | 5.0 | 0 |
| 15 | Budesonide | 8 | 0.0 | 91.5 | 0.5 | 0.0 | 99.5 | 0.5 | 0.1 | 9.9 |
| 16 | Budesonide | 8 | 0.0 | 91.5 | 0.5 | 50.0 | 49.5 | 0.5 | 0.1 | 9.9 |
| 17 | Budesonide | 8 | 0.0 | 91.5 | 0.5 | 99.5 | 0.0 | 0.5 | 0.1 | 9.9 |
| 18 | Budesonide | 8 | 50.0 | 41.5 | 0.5 | 0.0 | 99.5 | 0.5 | 0.1 | 9.9 |
| 19 | Budesonide | 8 | 50.0 | 41.5 | 0.5 | 50.0 | 49.5 | 0.5 | 0.1 | 9.9 |
| 20 | Budesonide | 8 | 50.0 | 41.5 | 0.5 | 99.5 | 0.0 | 0.5 | 0.1 | 9.9 |
| 21 | Budesonide | 8 | 91.5 | 0.0 | 0.5 | 0.0 | 99.5 | 0.5 | 0.1 | 9.9 |
| 22 | Budesonide | 8 | 91.5 | 0.0 | 0.5 | 50.0 | 49.5 | 0.5 | 0.1 | 9.9 |
| 23 | Budesonide | 8 | 91.5 | 0.0 | 0.5 | 99.5 | 0.0 | 0.5 | 0.1 | 9.9 |

Example 3

Example 3 was conducted expanding on Example 2 varying the amounts of leucine and sugar in the powders containing Budesonide as active agent (defined as HLSA Bud in the table). Together with the powders containing Budesonide, bulking agent powders were produced containing lactose and leucine at three different levels of leucine using lactose as filler to form the bulking agent (defined as BA in the table) i.e. of powder containing leucine and lactose but with no active agent.

The presence of leucine in three different amounts 0%, 50% and 91.5% serves to highlight the properties of disaggregating agent that this takes in the formulation with positive effects on parameters such as Delivered Fraction and Fine Particle Fraction.

Following preparation of the powders of Examples 12, 13 and 14, these were mixed with 3 types of Bulking Agent powders.

These 3 Bulking Agents also contain Leucine in three different amounts (0%, 50% and 99.5%)

TABLE 3B

| | Water content (%) | | Particle Size (μm) | | Active content % | |
|---|---|---|---|---|---|---|
| Ex. | T0 | T3 | T0 | T3 | T0 | T3 |
| 12 | 2.6 | 2.3 | 2.0 | 2.2 | 102.9 | 102.3 |
| 13 | 1.9 | 1.6 | 1.9 | 1.9 | 101.4 | 99.3 |
| 14 | 0.7 | 0.4 | 3.0 | 3.0 | 89.3 | 91.6 |
| 15 | 2.6 | 1.9 | 3.1 | 4.4 | 95.9 | 101.9 |
| 16 | 2.2 | 2.0 | 2.1 | 1.9 | 101.3 | 104.6 |
| 17 | 1.0 | 0.4 | 3.2 | 3.7 | 103.4 | 100.2 |
| 18 | 2.7 | 1.7 | 2.9 | 4.5 | 102.2 | 95.3 |
| 19 | 2.6 | 2.1 | 2.0 | 2.0 | 99.3 | 103.1 |
| 20 | 0.9 | 0.5 | 3.2 | 3.4 | 92.9 | 83.4 |
| 21 | 2.9 | 1.9 | 3.6 | 3.8 | 98.8 | 89 |
| 22 | 2.3 | 2.3 | 2.4 | 2.4 | 99.8 | 92.6 |
| 23 | 0.4 | 0.4 | 3.3 | 3.5 | 91.4 | 62.8 |

TABLE 3C

| | Degradation (%) | | | DF (%) | | FPF (%) | |
|---|---|---|---|---|---|---|---|
| Ex. | T0 | T3 | Growth | T0 | T3 | T0 | T3 |
| 12 | 0.0 | 0.0 | 0.0 | 73.7 | 73.6 | 45.8 | 37.9 |
| 13 | 0.4 | 0.7 | 0.3 | 79.1 | 79.0 | 67.6 | 74.4 |
| 14 | 1.6 | 4.4 | 2.8 | 92.6 | 93.1 | 69.6 | 78.5 |
| 15 | 0.0 | 0.4 | 0.4 | 94.3 | 94.6 | 35.5 | 24.0 |
| 16 | 0.0 | 0.4 | 0.4 | 92.9 | 94.7 | 44.1 | 40.0 |
| 17 | 0.0 | 1.9 | 1.9 | 96 | 96.0 | 44.3 | 33.7 |
| 18 | 0.4 | 0.7 | 0.3 | 95.6 | 95.6 | 44.3 | 27.2 |
| 19 | 0.4 | 1.5 | 1.1 | 94.4 | 95.5 | 64.6 | 75.2 |
| 20 | 0.4 | 13.2 | 12.8 | 96 | 95.8 | 57.5 | 65.6 |
| 21 | 1.7 | 3.0 | 1.3 | 95.9 | 95.6 | 47.2 | 18.5 |
| 22 | 1.7 | 5.6 | 3.9 | 92.3 | 95.7 | 51.3 | 72.0 |
| 23 | 1.8 | 23.7 | 21.9 | 95.8 | 97.0 | 47.2 | 79.4 |

According to the present invention the powder is acceptable, i.e. is considered within the optimal parameters for inhalation administration, when:

the degradation products are less than 1% of the total active agent, at the time T0 (degradation products T0<1% tot);

the Delivered Fraction (DF), i.e. the percentage of the dose of active agent delivered from the mouthpiece of the inhaler, is greater than 80% at the time T3 (ED % T3>80%);

the Fine Particle Fraction, i.e. the amount of fine particles less than 5.0 μm, is greater than 60% at the time T0 and at the time T3 (FPF T0 and T3>60%).

TABLE 4A

| | | HLSA FF (composition %) | | | | BA (composition %) | | | Powder mixture | |
|---|---|---|---|---|---|---|---|---|---|---|
| Ex | Active | Formoterol | Leucine | Lactose | Tween 80 | Leucine | Lactose | Tween 80 | HLSA Bud (mg) | BA (mg) |
| 24 | Formoterol | 2.25 | 0.0 | 97.25 | 0.5 | | | | 5.0 | 0.0 |
| 25 | Formoterol | 2.25 | 20.0 | 77.25 | 0.5 | | | | 5.0 | 0.0 |
| 26 | Formoterol | 2.25 | 97.25 | 0.0 | 0.5 | | | | 5.0 | 0.0 |
| 27 | Formoterol | 2.25 | 0.0 | 97.25 | 0.5 | 0.0 | 99.5 | 0.5 | 0.01 | 9.99 |
| 28 | Formoterol | 2.25 | 0.0 | 97.25 | 0.5 | 50.0 | 49.5 | 0.5 | 0.01 | 9.99 |
| 29 | Formoterol | 2.25 | 0.0 | 97.25 | 0.5 | 99.5 | 0.0 | 0.5 | 0.01 | 9.99 |
| 30 | Formoterol | 2.25 | 20.0 | 77.25 | 0.5 | 0.0 | 99.5 | 0.5 | 0.01 | 9.99 |
| 31 | Formoterol | 2.25 | 20.0 | 77.25 | 0.5 | 50.0 | 49.5 | 0.5 | 0.01 | 9.99 |
| 32 | Formoterol | 2.25 | 20.0 | 77.25 | 0.5 | 99.5 | 0.0 | 0.5 | 0.01 | 9.99 |
| 33 | Formoterol | 2.25 | 97.25 | 0.0 | 0.5 | 0.0 | 99.5 | 0.5 | 0.01 | 9.99 |
| 34 | Formoterol | 2.25 | 97.25 | 0.0 | 0.5 | 50.0 | 49.5 | 0.5 | 0.01 | 9.99 |
| 35 | Formoterol | 2.25 | 97.25 | 0.0 | 0.5 | 99.5 | 0.0 | 0.5 | 0.01 | 9.99 |

Example 4

The example was conducted by producing powders containing Formoterol Fumarate as active agent (defined as HLSA FF in the table) formulated with lactose and leucine in two different amounts.

Together with the powders containing Formoterol Fumarate, powders were produced containing lactose and leucine in three different amounts of leucine using lactose as filler to form a bulking agent (defined as BA in the table), i.e. of powder containing leucine and lactose but with no active agent.

The presence of leucine in three different amounts 0%, 50% and 91.5% serves to highlight the properties of disaggregating agent that this takes in the formulation with positive effects on parameters such as Delivered Fraction and Fine Particle Fraction.

Following preparation of the powders of Examples 12, 13 and 14, these were mixed with 3 types of Bulking Agent powders.

These 3 Bulking Agents also contain Leucine in three different amounts (0%, 50% and 99.5%).

This further part of the study highlights the capacity of the Bulking agent to promote complete emptying of the capsule.

Nevertheless, the composition of the Bulking agent is critical since a Bulking Agent that has too much leucine produces effects of chemical degradation of the active agent.

TABLE 4B

| | Water content (%) | | Particle Size (μm) | | Active content % | |
|---|---|---|---|---|---|---|
| Ex. | T0 | T3 | T0 | T3 | T0 | T3 |
| 24 | 4.2 | 3.6 | 2.5 | 2.85 | 96.6 | 97.4 |
| 25 | 3.3 | 3.3 | 1.5 | 1.33 | 100.3 | 95.3 |
| 26 | 0.8 | 0.6 | 2.6 | 2.59 | 95.2 | 89.3 |
| 27 | 2.8 | 1.7 | 3.4 | 3.98 | 98.8 | 90.5 |
| 28 | 3.2 | 2 | 2.0 | 2.12 | 98.5 | 97 |
| 29 | 0.7 | 0.3 | 3.3 | 3.59 | 95.5 | 86.1 |
| 30 | 2.6 | 1.8 | 3.1 | 3.88 | 97.2 | 88.9 |
| 31 | 2.4 | 1.7 | 2.1 | 2.16 | 96.8 | 101.5 |
| 32 | 0.6 | 0.4 | 2.8 | 3.52 | 92.7 | 76.5 |
| 33 | 2.6 | 2.3 | 3.3 | 3.82 | 78.7 | 73.2 |
| 34 | 2.4 | 1.8 | 2.1 | 2.17 | 84.6 | 87.8 |
| 35 | 0.4 | 0.2 | 3.2 | 3.52 | 93.6 | 68.8 |

TABLE 4C

| | Degradation (%) | | | DF (%) | | FPF (%) | |
|---|---|---|---|---|---|---|---|
| Ex. | T0 | T3 | Growth | T0 | T3 | T0 | T3 |
| 24 | 0.8 | 0.7 | 0.0 | 76.8 | 79.2 | 38.9 | 42.7 |
| 25 | 0.2 | 0.9 | 0.7 | 78.3 | 79.1 | 71.9 | 70.6 |
| 26 | 1.0 | 6.9 | 5.9 | 94.1 | 95.7 | 77.8 | 87.3 |
| 27 | 0.8 | 0.5 | 0.0 | 93.5 | 90.7 | 36.9 | 32.9 |
| 28 | 1.0 | 0.7 | 0.0 | 85.7 | 81.3 | 37.5 | 48.2 |
| 29 | 1.6 | 6.6 | 5 | 96.8 | 93.9 | 30.6 | 37.8 |
| 30 | 0.2 | 3.9 | 3.7 | 96.1 | 91.8 | 38 | 29.8 |

TABLE 4C-continued

| | Degradation (%) | | | DF (%) | | FPF (%) | |
|---|---|---|---|---|---|---|---|
| Ex. | T0 | T3 | Growth | T0 | T3 | T0 | T3 |
| 31 | 0.2 | 0.6 | 0.4 | 91.4 | 92.2 | 73.4 | 78.1 |
| 32 | 1.3 | 7.4 | 6.1 | 96.6 | 94 | 65.1 | 69.3 |
| 33 | 0.7 | 5.5 | 4.8 | 95 | 93 | 39.3 | 30.8 |
| 34 | 0.8 | 2.4 | 1.6 | 90.1 | 97.7 | 45.3 | 78.9 |
| 35 | 2.3 | 12.8 | 10.5 | 95.5 | 97.2 | 71.1 | 68.3 |

Example 5

The example was conducted producing formulations containing tiotropium bromide powders alone (defined as HLSA.Tio and standing for high loading single active of tiotropium) or powders containing a combination of tiotropium bromide together with formoterol fumarate as active agents (defined as HLDA.TioFF and standing for high loading double active of tiotropium and formoterol).

Together with the powders containing tiotropium or tiotropium and formoterol, a bulking agent powder was produced and obtained incorporating leucine, lactose and tween 80.

Following the preparation of the HLSA.Tio and the HLDA.TioFF these were mixed at two different dosing levels with different amounts of Bulking agent.

According to the present invention the powders are acceptable and within the acceptable parameters for optimal inhalation administration:

the Delivered Fraction (DF), i.e. the percentage of the dose of active agent delivered from the mouthpiece of the inhaler, is greater than 80% at the time T0 0;
the Fine Particle Fraction, i.e. the amount of fine particles less than 5.0 μm, is greater than 60% at the time T0.

TABLE 5A

| | | | HLSA.Tio/HLDA.TioFF (composition %) | | | | | BA (composition %) | | | Powder mixture | |
|---|---|---|---|---|---|---|---|---|---|---|---|---|
| | | | | | | | | | | | HLSA/HLDA | |
| Ex | Active | Active | Tiotropium | Formoterol | Leucine | Lactose | Tween 80 | Leucine | Lactose | Tween 80 | (mg) | BA (mg) |
| 36 | Titropium | | 3.0 | | 20.0 | 76.5 | 0.5 | 50.0 | 49.5 | 0.5 | 0.6 | 2.4 |
| 37 | Titropium | Formoterol | 3.0 | 3.0 | 20.0 | 73.5 | 0.5 | 50.0 | 49.5 | 0.5 | 0.6 | 2.4 |
| 38 | Titropium | | 3.0 | | 20.0 | 76.5 | 0.5 | 50.0 | 49.5 | 0.5 | 0.1 | 9.9 |
| 39 | Titropium | Formoterol | 3.0 | 3.0 | 20.0 | 73.5 | 0.5 | 50.0 | 49.5 | 0.5 | 0.1 | 9.9 |

TABLE 5B

| EX | Water content (%) T0 | Particle size (μm) T0 |
|---|---|---|
| 36 | 2.7 | 1.7 |
| 37 | 2.3 | 1.4 |
| 38 | 1.8 | 1.8 |
| 39 | 2.6 | 1.5 |

TABLE 5C

| EX | DF (%) Tiotropium T0 | DF (%) Formoterol T0 | FPF (%) Tiotropium T0 | FPF (%) Formoterol T0 |
|---|---|---|---|---|
| 36 | 85.1 | | 62.4 | |
| 37 | 87.4 | 88.4 | 61.3 | 64.3 |
| 38 | 92.4 | | 68.7 | |
| 39 | 93.2 | 93.1 | 69.5 | 66.7 |

The invention claimed is:

1. A pharmaceutical composition for inhalatory use in powder form, which is obtained by preparing
   a) a first powder comprising an active principle in an amount greater than 1% by weight of said first powder, leucine in amount from 18 to 55% by weight of said first powder and lactose in an amount from 40 to 80% by weight of said first powder;
   b) a second powder comprising leucine in amount from 18 to 55% by weight of said second powder and lactose in amount from 40 to 80% by weight of said second powder and being free of an active principle;
   c) blending said first powder and said second powder to form a single mixture;
   wherein said first powder is in an amount from 0.1 to 25% and said second powder is in an amount from 99.9 to 75% with respect to the total amount of the composition; and said composition has a fine particle fraction (FPF) greater than 60% and an delivered fraction (DF) greater than 80%.

2. The composition according to claim 1, wherein the ratio from the amount of the whole powder in amorphous form which form the composition expressed by weight, to the amount of lactose in the composition expressed in weight, is from 0.8 to 1.5.

3. The composition according to claim 1, wherein said first and second powders further comprise a surfactant in an amount from 0.2 to 2% by weight of each powder.

4. The composition according to claim 1, wherein said active principle is a hydrolysable active principle.

5. The composition according to claim 1, wherein said active principle is selected from the group consisting of inhalation bronchodilators with short and long duration of action, corticosteroids, anticholinergics, antibiotics, mucolytics, heparin and its derivatives, and antioxidant substances.

6. The composition according to claim 5, wherein said antioxidant substances are selected from the group consisting of N-acetylcysteine, Carnosine, Melatonin, Resveratrol, Ascorbic Acid, Alpha-tocopherol, Folic Acid, Trans-Caffeic Acid, Hesperidin, Epigallocatechin Gallate, Delphinidin, Acid Rosmainico, Myricetin, 5-methyltetrahydrofolic Acid, 5-formyltetrahydrofolic Acid, Astaxanthin, Lycopene, and Curcumin.

7. The composition according to claim 1, wherein comprising a third powder comprising an active ingredient in an amount greater than 1% by weight of said third powder, leucine in amount from 18 to 55% by weight of said third powder, a sugar in an amount from 40 to 80% by weight of said third powder.

8. The composition according to claim 3, wherein said surfactant is selected from the group consisting of benzalkonium chloride, cetrimide, docusate sodium, glyceryl monooleate, sorbitan esters, sodium lauryl sulfate, polysorbates, phospholipids, bile salts, polysorbates, block copolymers of polyoxyethylene and polyoxypropylene.

9. The composition according to claim 3, wherein said surfactant is in an amount from 0.4 to 0.8% by weight of each powder.

10. The composition according to claim 7, wherein said sugar is selected from the group consisting of lactose, trehalose, sucrose and maltodextrin.

11. The composition according to claim 1, wherein said powders have a X50 less than 5μm.

12. A kit for the administration of a drug as inhalatory powder, comprising a metered amount of the composition according to claim 1 and a device for inhalation.

13. The composition according to claim 2, wherein said first and second powder comprise a surfactant in an amount from 0.2 to 2% by weight of each powder.

14. The composition according to claim 2, wherein said active principle is a hydrolysable active principle.

* * * * *